(12) United States Patent
Yu et al.

(10) Patent No.: US 8,403,823 B2
(45) Date of Patent: Mar. 26, 2013

(54) VENTRICULAR CONNECTOR

(75) Inventors: Long Sheng Yu, Coral Springs, FL (US); Peter Piferi, Plantation, FL (US); Steven M. Parnis, Granite Bay, CA (US)

(73) Assignee: Heartware Inc., Miami Lakes, FL (US)

( * ) Notice: Subject to any disclaimer, the term of this patent is extended or adjusted under 35 U.S.C. 154(b) by 1064 days.

(21) Appl. No.: 10/799,534

(22) Filed: Mar. 12, 2004
(Under 37 CFR 1.47)

(65) Prior Publication Data
US 2004/0171905 A1    Sep. 2, 2004

Related U.S. Application Data

(62) Division of application No. 10/184,481, filed on Jun. 26, 2002, now Pat. No. 6,732,501.

(51) Int. Cl.
*A61M 1/12* (2006.01)
(52) U.S. Cl. ............................ 600/16; 623/3.26; 607/115
(58) Field of Classification Search .................... 623/3.2; 600/16
See application file for complete search history.

(56) References Cited

U.S. PATENT DOCUMENTS

| | | | |
|---|---|---|---|
| 3,766,567 A * | 10/1973 | Kahn et al. .................... | 623/3.21 |
| 4,004,298 A | 1/1977 | Freed | |
| 4,086,665 A * | 5/1978 | Poirier .......................... | 623/1.44 |
| 4,118,806 A | 10/1978 | Porier et al. | |
| 4,310,001 A | 1/1982 | Comben | |
| 4,769,031 A | 9/1988 | McGough et al. | |
| 5,405,339 A | 4/1995 | Kohnen et al. | |
| 5,613,935 A | 3/1997 | Jarvik | |
| 5,722,429 A | 3/1998 | Larson, Jr. et al. | |
| 5,766,042 A | 6/1998 | Ries et al. | |
| 5,810,708 A | 9/1998 | Woodard et al. | |

(Continued)

OTHER PUBLICATIONS

Article "A New Connector System for Total Artificial Hearts" in vol. III 111, Trans Am Soc. Artif Intern Organs 1987, pp. 151-156.

(Continued)

*Primary Examiner* — Niketa Patel
*Assistant Examiner* — Alyssa M Alter
(74) *Attorney, Agent, or Firm* — John P. White; Cooper & Dunham LLP (57) ABSTRACT

A ventricular apex connector for quick connection and disconnection of an inflow tube of a ventricular assist device, comprising a sewing ring, a cylindrical ring, gripping pins, a spring ring and a sealing O-ring is provided. The cylindrical ring defines two openings, diametrically opposed to each other, in its walls. Gripping pins, comprising rods with gripping pads, are placed in the openings in the cylindrical ring so that the gripping pads are at rest within the inner circumference of the cylindrical ring. The spring ring is placed around the cylindrical ring and the rods of the gripping pads, which extend out of the outer wall of the cylindrical ring, are welded to the spring ring. The gripping pins are thus biased towards each other by the force of the spring ring. When the spring ring is squeezed, at points away from the gripping pin connection points, the deformation of the spring ring causes the gripping pads to be pulled out towards the inner wall of the cylindrical ring. An inflow tube of a heart pump may then be inserted into the ventricular apex connector, and upon the release of the spring ring, the inflow tube is sealedly held within the ventricle of the heart. In an embodiment an adapter sleeve may be attached to the inflow tube. In a further embodiment, the inflow tube may include an inner sleeve that is slidably and rotatably mounted therein. The inflow tube may have a bend at an end.

9 Claims, 5 Drawing Sheets

U.S. PATENT DOCUMENTS

| | | | |
|---|---|---|---|
| 5,814,005 A | | 9/1998 | Barra et al. |
| 5,866,217 A | * | 2/1999 | Stenoien et al. ............. 623/1.44 |
| 6,001,056 A | * | 12/1999 | Jassawalla et al. ............. 600/16 |
| 6,290,639 B1 | * | 9/2001 | Mussivand et al. ............. 600/16 |
| 6,346,071 B1 | | 2/2002 | Mussivand |

OTHER PUBLICATIONS

Article "Implantable Axial Flow Impeller Pumps" in Journal of Circulatory Support (1998), vol. 1, Nos. 13-19. pp. 13-19.

* cited by examiner

VENTRICULAR CONNECTOR

This application is a division of application Ser. No. 10/184,481 filed on Jun. 26, 2002 now U.S. Pat. No. 6,732,501.

FIELD OF THE INVENTION

The present invention concerns a connector to allow an inflow tube of a blood pump to be securely fastened to the heart.

BACKGROUND OF THE INVENTION

Clinical application of ventricular assist devices to support patients with end-stage heart disease as a bridge to cardiac transplantation or as an end stage therapeutic modality has become an accepted clinical practice in cardiovascular medicine. It is estimated that greater than 35,000 persons suffering from end stage cardiac failure are candidates for cardiac support therapy.

Currently, several ventricular assist devices are used clinically, and several more are undergoing development. In most of these devices, blood enters the device via an inflow tube, which is placed within the ventricular cavity. A sewing ring is usually attached to the ventricular apex of the heart and an inflow tube of a blood pump is inserted through the sewing ring and into the ventricle. The blood pump is then secured to the sewing ring by placing a ligature, or tie, around the inflow tube of the pump and the sewing ring and tightening them together. A nylon band can also be placed around the sewing ring collar and tightened down on the inflow tube. By this method an adequate seal can be made and the pump and inflow tube are held in place. However, this method makes it very difficult to change the orientation of the inflow tube, or if necessary, to remove the inflow tube from the ventricle. Additionally, placing and tightening a nylon band and ligatures around the inflow tube can be difficult and comprises extra steps in the implant process.

Presently, there are some connection devices that use multiple screw type connectors, for ventricular assist devices on the outflow side. On the inflow side, the ligature tie method and devices have generally been used as well as some screw type connection devices. With total artificial hearts, various screw type devices, twist-lock devices, and snap on connectors have been used. All of these connectors have the disadvantage of requiring the use of two hands to install. Further, in the area where these devices must be installed, space is very limited and installation of these devices is difficult.

It is therefore an object of the present invention to provide an easy to use quick connect and disconnect device for connecting a tube to a patient's heart.

It is another object of the present invention to provide a device that provides a seal in the connection of a tube to a heart and allows for easy rotation of the orientation of a tube of a blood pump, after insertion into a heart.

It is a further object of the present invention to provide an adapter sleeve for attachment to a tube of a blood pump in order to accommodate different sized hearts and pumps.

Other objects and advantages of the present invention will become apparent as the description proceeds.

SUMMARY OF THE INVENTION

In accordance with the present invention, a connector for connecting an inflow tube of a ventricular assist device to a heart is provided. The connector comprises a first member for attachment to a heart, a gripping member adapted for receiving the inflow tube, the gripping member being adapted for coupling to the first member. A second member is provided, for enabling hand manipulation of the gripping member, to permit an operator to open the gripping member to enable the inflow tube to be received and gripped by the gripping member.

In the illustrative embodiment, the connector of the present invention is designed to be attached to the ventricular apex of a heart. The first member is a sewing ring adapted to be sewed to the heart. The gripping member comprises a cylindrical ring defining two openings in its wall, diametrically opposed to each other, through which gripping rods are disposed. A gripping head, which comprises a titanium metal pad having grip teeth to assist in holding, is coupled to each gripping rod such that the gripping head is disposed within the area defined by the cylindrical ring.

In the illustrative embodiment the second member is a spring ring, composed of titanium, which surrounds the cylindrical ring in a concentric ring relationship. The gripping rods are attached to the spring ring and the gripping heads are, as a result, biased towards each other and the center of the area defined by the cylindrical ring, when the spring ring is in a first, at rest, position. The gripping rods, which are also made of titanium, are attached to the spring ring by welding. When the spring ring is squeezed, at points away from the points of connection of the gripping pins, the deformation of the spring ring causes the gripping pins to be pulled back allowing an inflow tube of a ventricular assist device to be inserted into the connector. Releasing the spring ring causes the gripping pins to move towards their first position until they engage the inflow tube. Further squeezing of the spring ring causes the release of the gripping pins from the inflow tube to allow the inflow tube to be adjusted, manipulated or withdrawn.

In the illustrative embodiment, an O-ring seal is provided for insertion into a groove in the cylindrical ring. The O-ring may be installed in the cylindrical ring so as to form a leak proof seal between the inflow tube and the ventricle apex connector. In the illustrative embodiment, the inflow tube of the ventricular assist device is provided with a textured surface to facilitate the gripping of the tube by the gripping members.

In an alternate embodiment a ventricular assist device for a heart is provided which comprises a pump portion, an inflow tube protruding from the pump portion and an adapter sleeve of a first predetermined length attached to the inflow tube forming an extended inflow tube having a total length greater than the first predetermined length. The adapter sleeve may include a first end having a coupling in order to attach the adapter sleeve to a ventricular apex of a heart. The adapter sleeve may have the coupling attached to a sewing ring that is attached to the ventricular apex. The adapter sleeve may be formed of a smooth cylinder of titanium. The adapter sleeve may include cylindrical grooves forming perforations on the surface of the sleeve wherein the sleeve may be separated along said grooves. The adapter sleeve may be formed of ceramic. The adapter sleeve may include a gripping member for attaching the extended inflow tube to the ventricular apex.

In a further alternate embodiment an inflow tube includes a bent end, an extendable end and/or a rotatable end. The inflow tube may include an inner sleeve that is rotatably and slidingly mounted therein in order to allow for the positioning of the tube in variable locations in the assisted organ.

A more detailed explanation of the invention is provided in the following description and claims and is illustrated in the accompanying drawings.

DETAILED DESCRIPTION OF THE ILLUSTRATIVE EMBODIMENT

Figure 1:
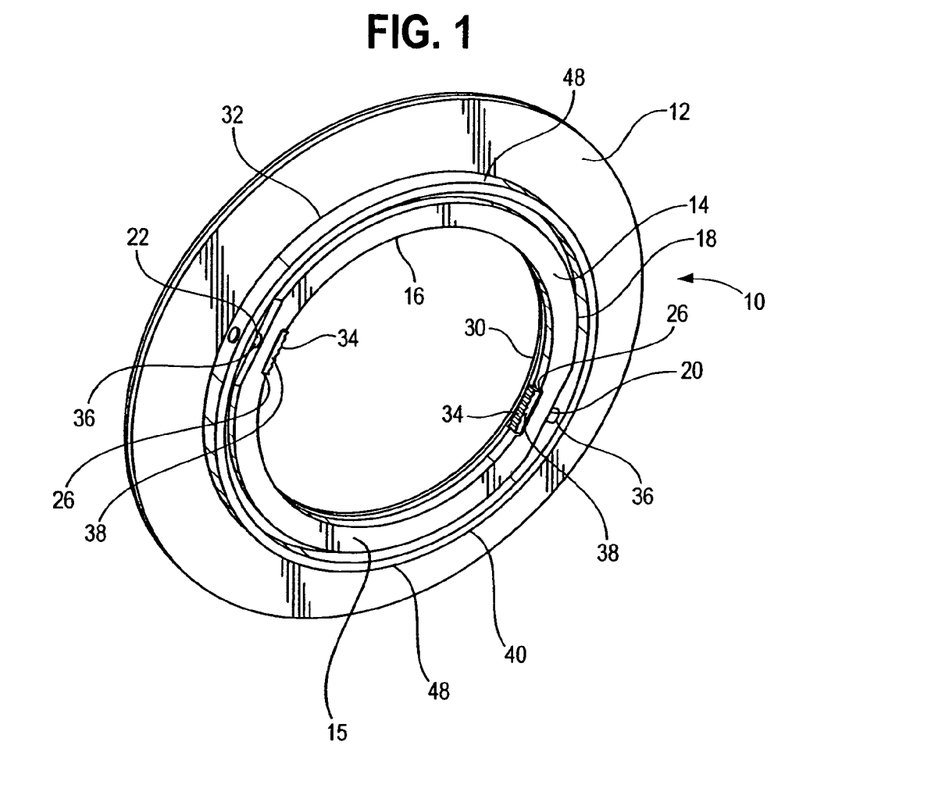
FIG. 1 is a perspective view of a ventricular apex connector made in accordance with the present invention.

Referring to the drawings, FIG. 1 shows a ventricular apex connector 10 having a sewing ring 12 and a cylindrical ring 14. Sewing ring 12 may be formed of fabric, such as polyester velour or other types of polyester material, expanded polytetrafluoroethylene (EPTFE) or other such fabrics which are well known in the art. Sewing ring 12 is adapted for attachment to the ventricular apex of the heart by surgical stitching, stapling or adhesives.

Figure 2:
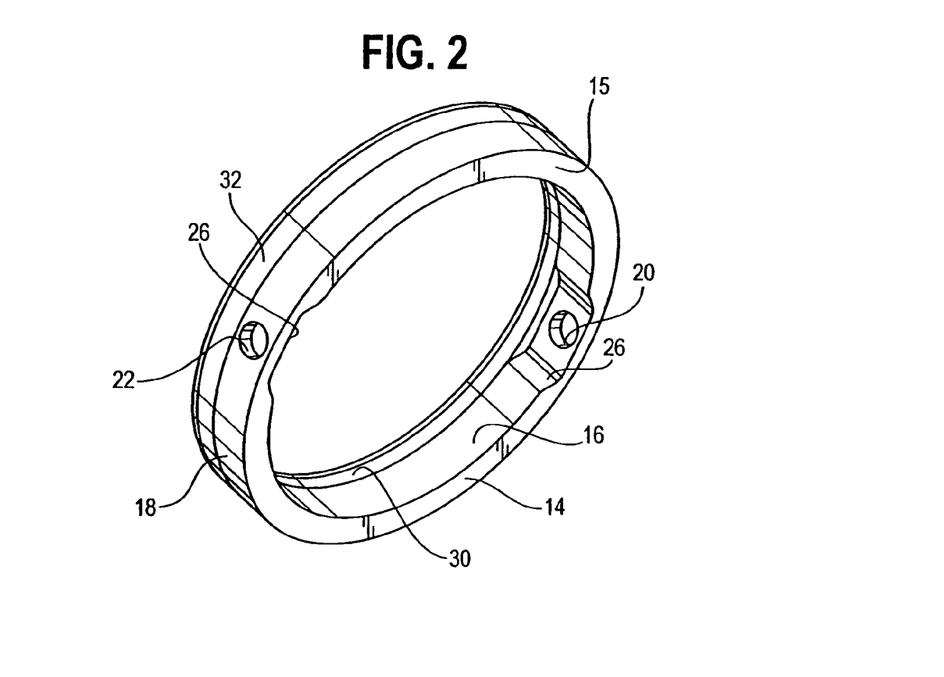
FIG. 2 is a perspective view of the cylindrical ring of the ventricular apex connector of FIG. 1.
Figure 5:
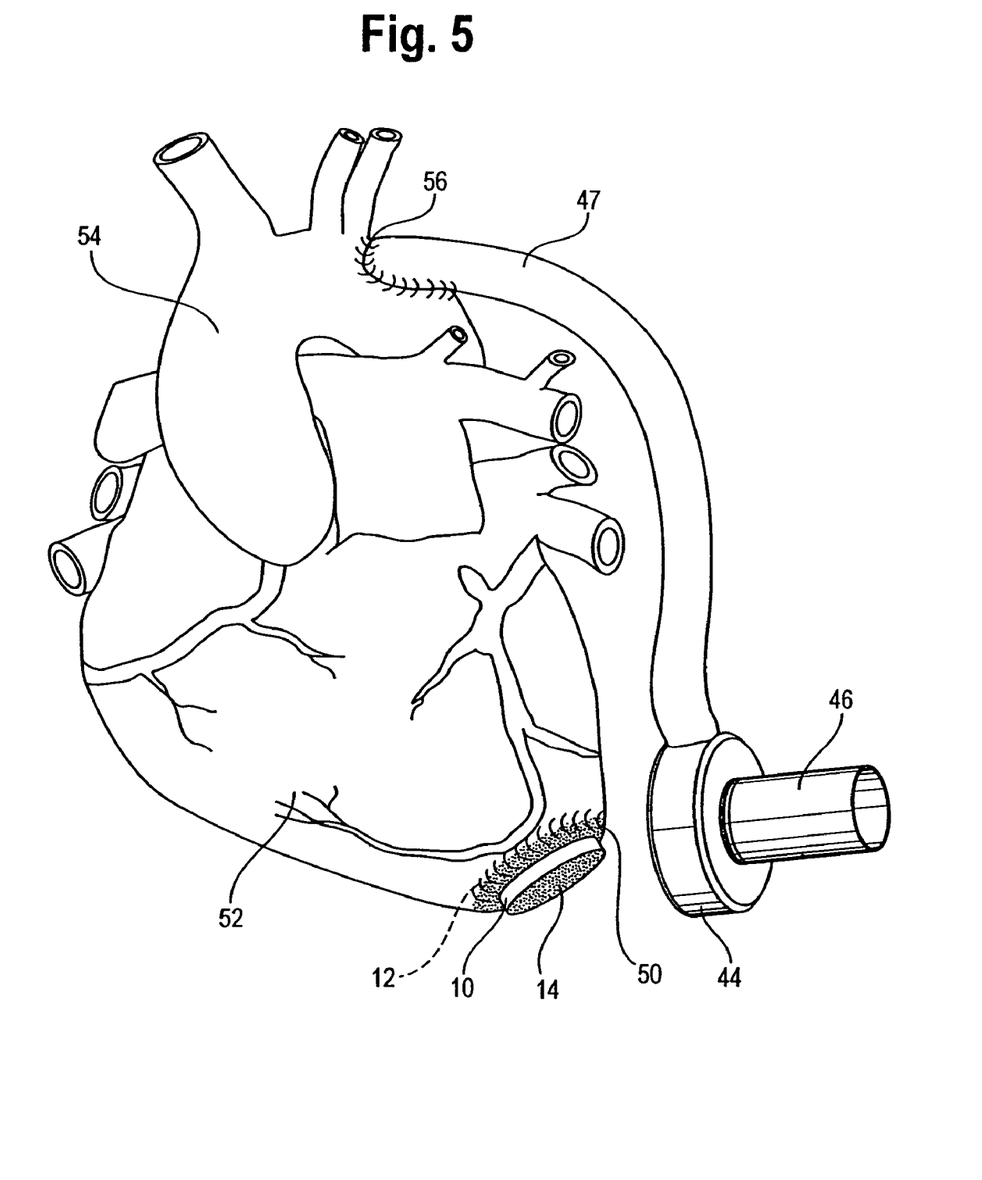
FIG. 5 is a perspective view of a heart to which a device made in accordance with the present invention has been attached.

As can be seen in FIG. 2, cylindrical ring 14 comprises a tube 15 having an inner wall 16 and an outer wall 18. Inner wall 16 is of a diameter slightly larger than the outer diameter of an inflow tube 19 of a ventricular assist device 44 (FIG. 3) which is to be connected to a heart 52 (FIG. 5). Cylindrical ring 14 defines openings 20 and 22 through tube 15. Openings 20 and 22 are defined, in the illustrative embodiment, generally in positions diametrically opposed to each other. It is to be understood, however, that openings 20 and 22 may be defined in numerous other positions, in other than diametric opposed relation to each other, without departing from the novel scope of the present invention. The utility of openings 20 and 22 will be discussed in detail below.

Inner wall 16 of cylindrical ring 14 defines two generally U-shaped cutouts 26, in tube 15, about openings 20 and 22. Inner wall 16 further defines a sealing groove 30, in which an O-ring 42 (FIG. 3) is inserted. Outer wall 18 defines a sewing ring groove 32 to facilitate connection of cylindrical ring 14 to sewing ring 12. Sewing ring 12 may be connected to cylindrical ring 14 in any conventional manner, such as screwing or pressure fit. In the illustrative embodiment, cylindrical ring 14 is constructed of titanium, but it is to be understood that cylindrical ring 14 may be made of any other metal, plastic or other rigid material, without departing from the novel scope of the present invention.

Referring again to FIG. 1, gripping pins 34, comprising rods 36 and gripping pads 38, extend through openings 20 and 22 of cylindrical ring 14, such that gripping pads 38 fit into cutouts 26. A spring ring 40 (FIG. 3), having a diameter larger than the diameter of cylindrical ring 14, is placed concentrically to cylindrical ring 14. Spring ring 40 is preferably constructed of titanium but may be made of any elastic material that may be temporarily deformed and subsequently returns to its original cylindrical shape. Rods 36 of gripping pins 34 are attached to spring ring 40. In the illustrative embodiment, rods 36 and gripping pins 34 are constructed of titanium, but it is to be understood that various other materials, such as steel, aluminum, or other metal or plastic materials may be used without departing from the novel scope of the present invention. Further, in the illustrative embodiment, gripping rods 36 are welded to spring ring 40. However, it is to be understood that any means of permanent attachment, including the use of adhesives or fasteners such as rivets or screws, may be used to attach gripping pins 34 to spring ring 40. When spring ring 40 and gripping pins 34 are attached together, gripping pins 34 are biased towards each other by spring ring 40.

Figure 3:
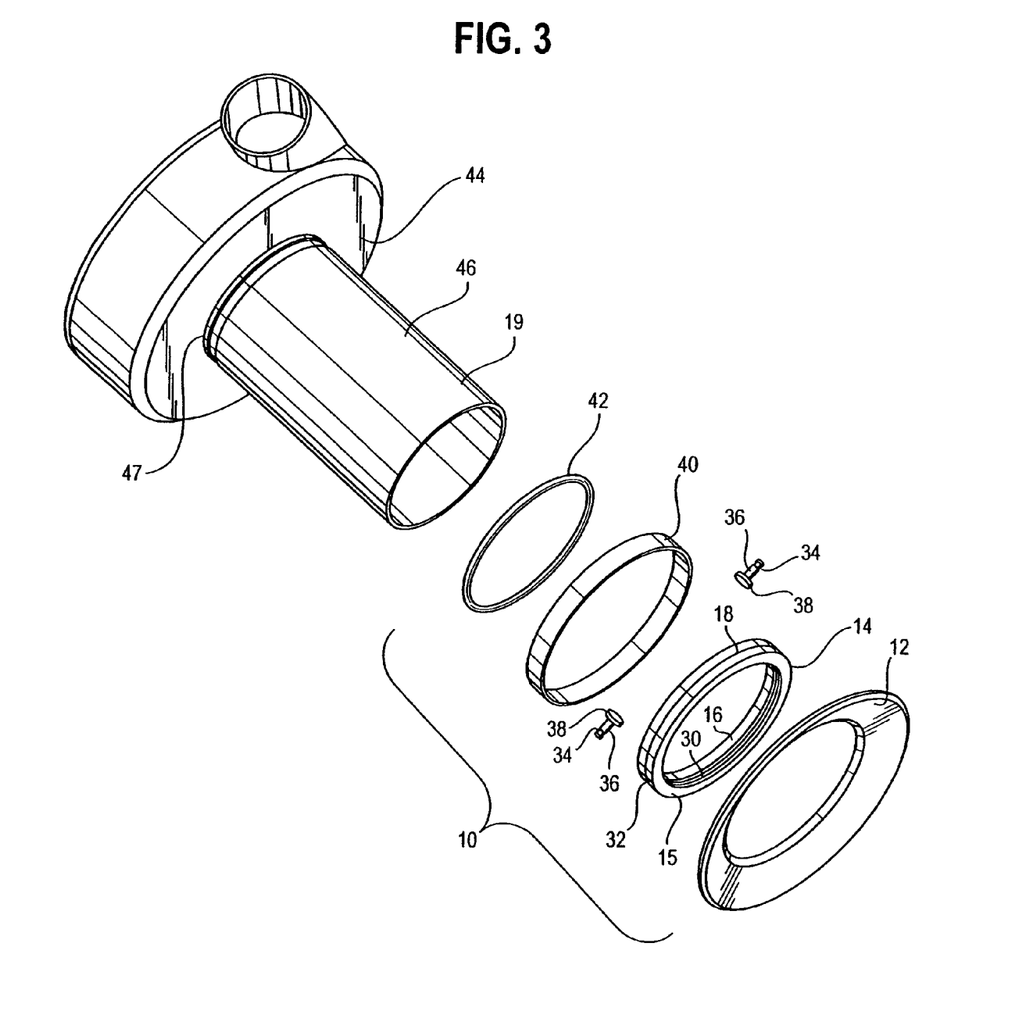
FIG. 3 is an exploded view of the ventricular apex connector of FIG. 1, in relationship to a blood pump.
Figure 4:
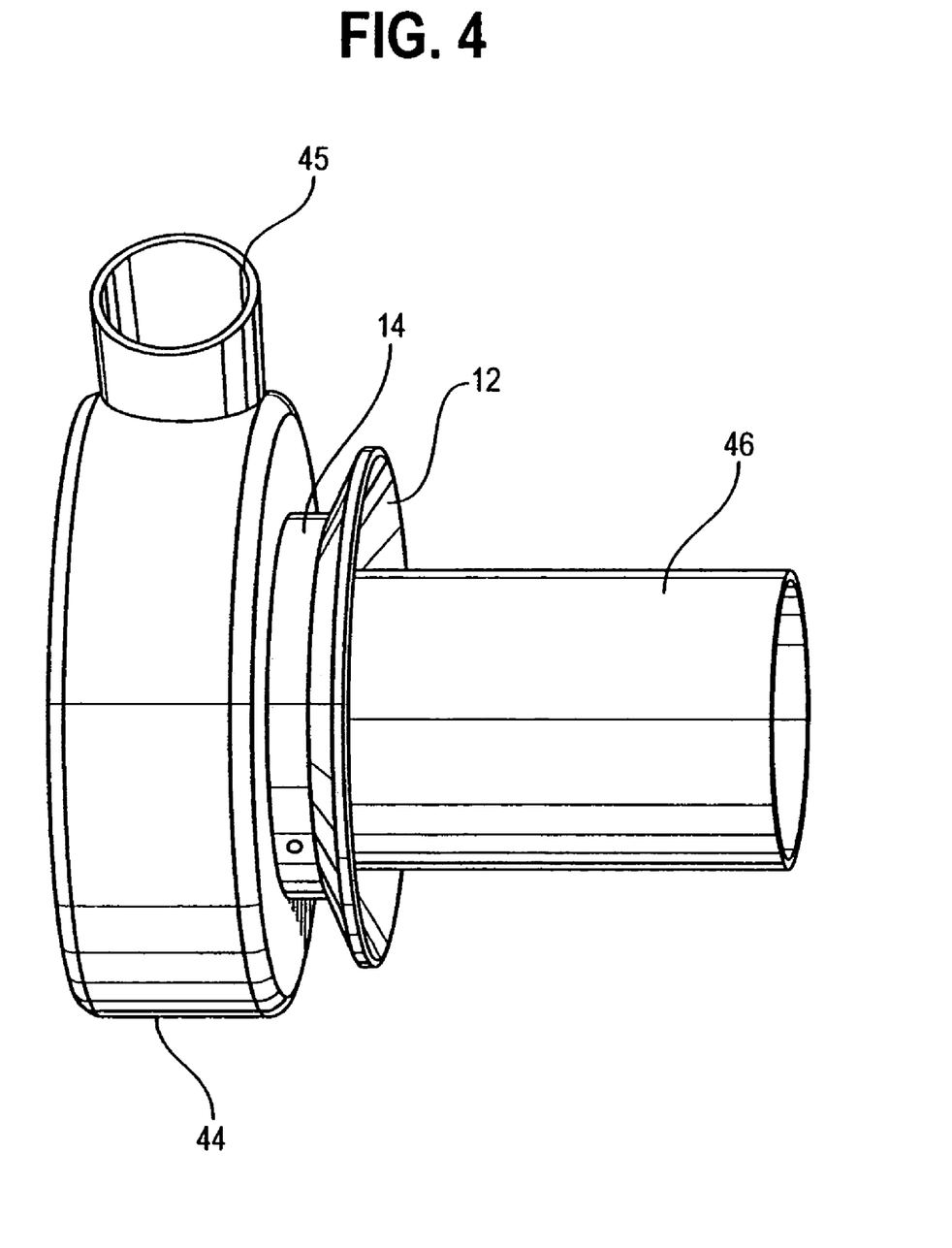
FIG. 4 is a perspective view of a ventricular apex connector made in accordance with the present invention attached to a blood pump.

An O-ring 42 is placed within sealing ring 30, of tube 15, to provide a generally leak proof seal. O-ring 42 is constructed of an elastic sealing material.

In the operation of the illustrative embodiment of a ventricular apex connector 10, when ventricular assist device 44 having inflow tube 46 and an outlet port 45 is to be associated with a heart 52, sewing ring 12 is secured to the ventricular apex 50 of a heart 52, as shown in FIG. 5. Spring ring 40 is squeezed, preferably at locations 48 (FIG. 1) on the circumference of spring ring 40, causing spring ring 40 to be deformed such that gripping pins 34 are pulled away from each other, into cutouts 26 of cylindrical ring 14. Inflow tube 46, of ventricular assist device 44, may then be inserted into cylindrical ring 14. When inflow tube 46 has been placed in the desired location within heart 52, spring ring 40 may be released, causing gripping pins 34 to move towards each other until gripping pads 38 contact inflow tube 46, at surface 47. In the illustrative embodiment surface 47 is textured to provided assistance in forming a tight friction fit between gripping pins 34 and the walls of inflow tube 46. Sealing is provided by O-ring 42. Gripping pads 34 hold the inflow tube securely, such that the body of ventricular assist device 44 is pressed tightly against the top of connector 10. FIG. 5 further shows that ventricular assist device 44 is in communication with heart 52, through a collapsible conduit 47 which communicates between outlet port 46 and the aorta 54 by means of a sutured connection 56.

If repositioning (such as for a change of orientation) or removal of inflow tube 46 is desired, spring ring 40 may be squeezed, again, at points 48, so that inflow tube 46 is released by gripping pins 34. Upon completion of removal of inflow tube 46, or its repositioning, spring ring 40 may again be released.

It can be seen that a novel device has been provided that allows for the quick installation of a flow tube to the heart, or other organ. The illustrated embodiment of the present invention enables the connection of an inflow tube using one hand. The present invention provides a seal so that leaking does not occur and enables the quick removal of the inflow tube and permits the easy change of orientation of the inflow tube.

Figure 6:
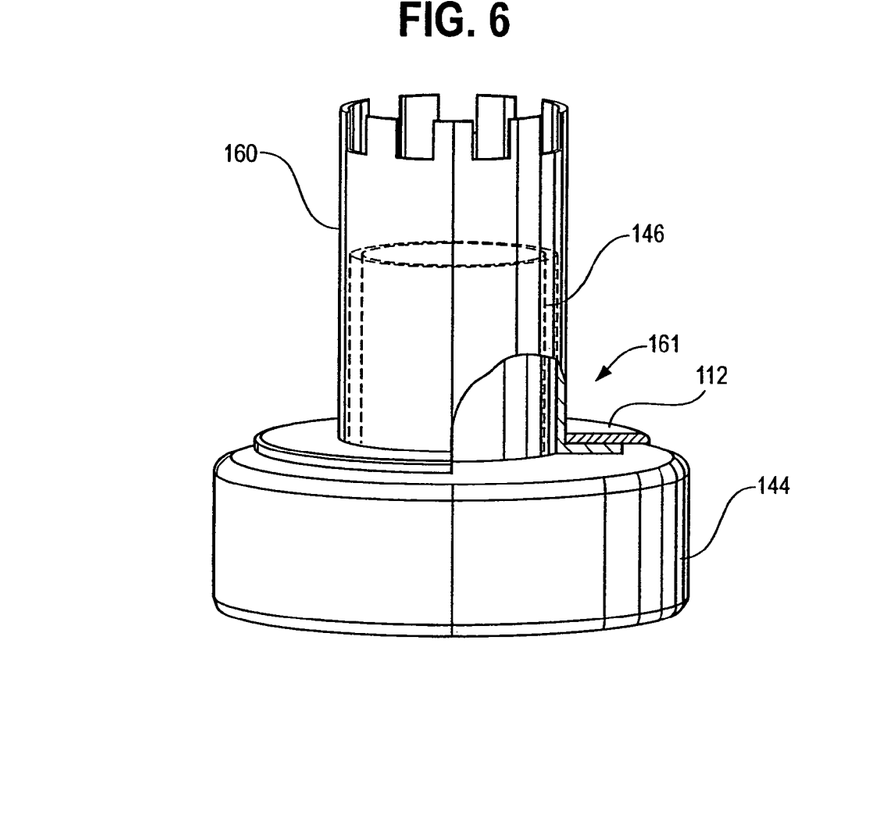
FIG. 6 is a plan view of an alternate embodiment of the present invention with an adapter sleeve.

FIG. 6 discloses and alternate embodiment of the present invention. A ventricular assist device 144 is provided having an inflow tube 146 and mounted thereon is a cylindrically-shaped adapter sleeve 160. A sewing ring 112 is provided that is adapted for attachment to the ventricular apex of the heart by surgical stitching, stapling or adhesives and is attached to a first end 161 of the sleeve adapter 160 via a bayonet type coupling. Other means of attaching the sleeve 160 to the sewing ring 112 may also be provided such as by threaded interior and exterior surfaces, fasteners or adhesives. The sewing ring 112 in an embodiment may be formed of fabric having a hard center portion of metal or polymer material to which the sleeve 160 is secured.

The adapter sleeve 160 may be formed of metal such as titanium. As discussed above the sleeve 160 is attached to the ventricular apex of the heart via the sewing ring 112. The adapter sleeve 160 may also be attached to the inflow tube 146 by mechanical means such as a bayonet type coupling, interference fit, threaded coupling or with fasteners. The attachment means may include an adjustable member to cause the sleeve 160 to extend or retract from the end of the inflow tube 146. The adapter sleeve 160 allows for the inflow tube 146 to be manufactured having a consistent length regardless of its application. For example, the width of the wall of the ventricle of the heart may vary by 8 mm to 18 mm from patient to patient. By use of the adapter sleeve 160, no modification of the inflow tube 146 is necessary. Having different sized adapter sleeves 160 available allows for variation in its attachment to the ventricular apex. For example, by extending the adapter sleeve 160, the device 144 and inflow tube 146 may be oriented at an angle offset from a perpendicular position with respect to the surface of the ventricle in order to maximize fluid flow. Such modification of the assist device 144 could be accomplished ahead of time or during the surgical implantation of the device, where the surgeon has multiple sizes of adapter sleeves 160 available depending on the thickness of the ventricular wall and also the space between the heart and other organs that is available for the assist device 144. The adapter sleeve 160 may have a first predetermined length from 15 mm. to 35 mm. The sleeve 160 is attached to the inflow tube and forms an extended inflow tube assembly having a total length greater than the first predetermined length of the sleeve 160. For example, in a preferred embodiment the total length of the extended inflow tube is 15 mm or less. The adapter sleeve 160 may also function as a receiver or extender. In such a way the adapter sleeve 160 may insure that the inflow tube 146 combined with the adapter sleeve 160 is the proper length to avoid in growth, stagnant blood or obstruction from other areas of the heart.

As well, the adapter sleeve 160 may include in an embodiment a crowned top having apertures 171 forming troughs 173 and crests 175 so that blood flow is not impeded if the end of the sleeve 160 abuts against a tissue or opposite wall of the heart. Other embodiments may include holes formed near the upper edge of the sleeve 180. As well, such a crowned top or holes may provide on the inflow tube 146 or 46 of the previous embodiments not having an adapter sleeve or at end 252 of the embodiment of FIG. 7. The number, width and depth of the crests may vary in accordance with the desired blood flow rate.

In an alternate embodiment, the sleeve 160 may be attached directly to the ventricular apex of the heart. In a further alternate embodiment the sleeve 160 may have cylindrical grooves or perforations axially spaced along the sleeve 160 to allow for each axial section to be peeled away in order to shorten the length of the sleeve 160. Such a sleeve 160 could be formed of a ceramic material that can be manipulated and separated without special tools. In this way, only a single sleeve need be present during an implantation procedure and upon determination of the proper size of the sleeve, modification may be effected on the spot. In another alternate embodiment, the adapter sleeve 160 may be combined with the above discussed gripping member or spring ring 40.

Figure 7:
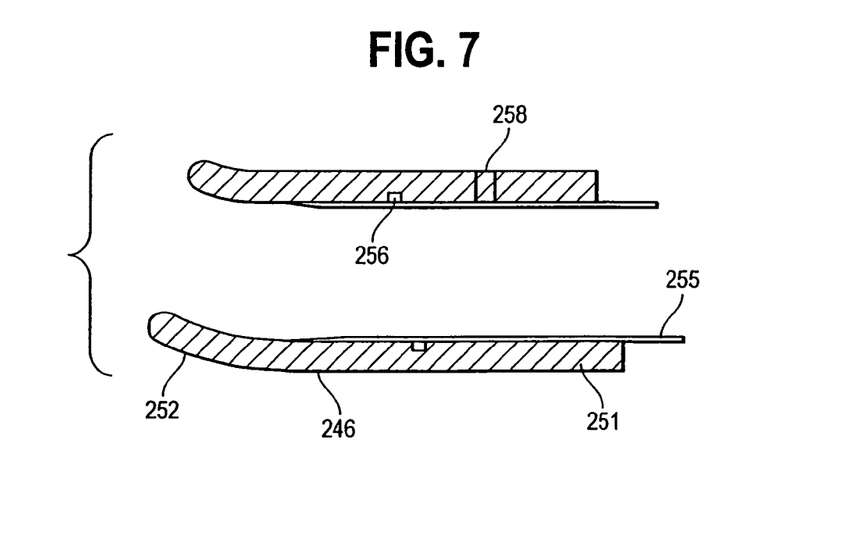
FIG. 7 is a sectioned view of an alternate embodiment of a flexible inflow tube.

Turning to FIG. 7, an alternate embodiment of the invention is depicted. An inflow tube 246 is provided having a first end 251 and a second end 252. The inflow tube may be formed of a metal such as titanium. The tube 246 includes an inner sleeve 255 that may be formed of metal such as titanium. The inner sleeve 255 is attached to the tube 246 via fastener 256 such as an O-ring that allows for the inner sleeve 255 to be rotatably and slidingly secured within the inner diameter of the tube 246. In an embodiment the tube is formed having a bend at its first end 252 which may be attached to the heart by a sewing ring, for example.

The first end 252 is inserted into the ventricle of the heart, or other assisted organ. The tube 246 may be rotated so that during an operation the insertion and attachment of the bent end 252 of the tube 246 to the heart can be accomplished more easily and also so that modifications may be made to the orientation of the tube in order to increase the flow rate. A surgeon may desire to locate the inflow tube at a location on the left ventricle, for example, where the highest rate of blood flow will occur. Once the inflow tube 246 is positioned with the inner sleeve 255 extended and rotated to its preferred position the assembly may be locked in position with a locking mechanism 258 such as a screw or other fastener. For example, in an embodiment a screw 258 may be tightened with a finger or screw driver in order to apply sufficient pressure against the wall of the inner sleeve 255 so that it is frictionally secured within the tube 246. As well, since each patient's assisted organ may be of slightly different size and shape, the flexible inflow tube 246 allows for accommodation of such variances when mounting the pump which is attached at the second end 251 of the inflow tube 246.

Although illustrative embodiments of the invention have been shown and described, it is to be understood that various modifications and substitutions may be made by those skilled in the art without departing from the novel spirit and scope of the invention.

What is claimed:

1. An apparatus comprising:
a cylindrical sleeve having an inner wall portion configured to extend over and form a seal against a standard sized ventricular assist pump inflow tube, the cylindrical sleeve forming an extended inflow tube configured to pass through a heart wall having a thickness;
the cylindrical sleeve having a length greater than a standard sized ventricular assist pump inflow tube length;
perforations in the cylindrical sleeve configured to allow breaking off a portion of the cylindrical sleeve to provide predetermined length adjustments; and
a coupling portion configured to attach the cylindrical sleeve to a ventricular apex of a heart.

2. The apparatus of claim 1, wherein the predetermined length adjustments are configured to match different heart wall thicknesses.

3. The apparatus of claim 1, wherein the coupling portion includes a sewing ring attached to the cylindrical sleeve and configured to connect to a ventricular apex of a heart by surgical stitching.

4. The apparatus of claim 1, wherein the coupling portion includes a textured surface for engagement with a ventricular apex connector.

5. The apparatus of claim 4, wherein the ventricular apex connector has an inside diameter configured for sealingly engaging with an outside diameter surface of the cylindrical sleeve.

6. The apparatus of claim 5, wherein the ventricular apex connector includes a cylindrical ring having at least two apertures.

7. The apparatus of claim 6, wherein the ventricular apex connector includes at least two gripping rods, each of the at least two gripping rods being disposed through one of the at least two apertures.

8. The apparatus of claim 7, wherein the ventricular apex connector includes at least two gripping pads, each of the at least two gripping pads connected to one of the at least two gripping rods and being positioned within an area defined by the cylindrical ring.

9. The apparatus of claim 8, wherein the ventricular apex connector includes a spring ring, the spring ring concentrically surrounding the cylindrical ring and attached to the at least two gripping rods at an end opposite the at least two gripping pads.

* * * * *

UNITED STATES PATENT AND TRADEMARK OFFICE
CERTIFICATE OF CORRECTION

| | | |
|---|---|---|
| PATENT NO. | : 8,403,823 B2 | Page 1 of 1 |
| APPLICATION NO. | : 10/799534 | |
| DATED | : March 26, 2013 | |
| INVENTOR(S) | : Yu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this
Eighteenth Day of November, 2014

Michelle K. Lee
*Deputy Director of the United States Patent and Trademark Office*